United States Patent
Qian et al.

(10) Patent No.: US 9,408,781 B2
(45) Date of Patent: Aug. 9, 2016

(54) DENTAL RESIN MODIFIED GLASS-IONOMER COMPOSITION

(71) Applicant: Kerr Corporation, Orange, CA (US)

(72) Inventors: Xuejun Qian, Foothill Ranch, CA (US); Xiangxu Chen, Diamond Bar, CA (US)

(73) Assignee: Kerr Corporation, Orange, CA (US)

( * ) Notice: Subject to any disclaimer, the term of this patent is extended or adjusted under 35 U.S.C. 154(b) by 291 days.

(21) Appl. No.: 13/764,717

(22) Filed: Feb. 11, 2013

(65) Prior Publication Data

US 2014/0228474 A1    Aug. 14, 2014

(51) Int. Cl.
*A61K 6/08* (2006.01)
*A61K 6/00* (2006.01)
*A61K 6/027* (2006.01)
*A61K 6/083* (2006.01)

(52) U.S. Cl.
CPC .............. *A61K 6/0091* (2013.01); *A61K 6/027* (2013.01); *A61K 6/083* (2013.01); *A61K 6/0835* (2013.01)

(58) Field of Classification Search
CPC .................................................. A61K 6/0835
USPC ........................................................ 523/116
See application file for complete search history.

(56) References Cited

U.S. PATENT DOCUMENTS

| | | | |
|---|---|---|---|
| 4,089,830 A | 5/1978 | Tezuka et al. | |
| 4,792,632 A | 12/1988 | Ellrich et al. | |
| 5,063,257 A | 11/1991 | Akahane et al. | |
| 5,130,347 A * | 7/1992 | Mitra | 522/149 |
| 5,154,762 A | 10/1992 | Mitra et al. | |
| 5,925,715 A | 7/1999 | Mitra | |
| 6,214,101 B1 | 4/2001 | Nakaseko | |
| 6,765,038 B2 | 7/2004 | Mitra | |
| 6,872,244 B2 | 3/2005 | Kobayashi et al. | |
| 2006/0247330 A1 | 11/2006 | Takano et al. | |
| 2007/0203257 A1* | 8/2007 | Qian | 523/116 |
| 2010/0090157 A1* | 4/2010 | Rao et al. | 252/79.1 |
| 2010/0292360 A1* | 11/2010 | Jia | A61K 6/0017 522/109 |
| 2011/0245368 A1 | 10/2011 | Yarimizu et al. | |

FOREIGN PATENT DOCUMENTS

EP    0329268 A2    8/1989

OTHER PUBLICATIONS

European Patent Office, Search Report and Preliminary Opinion issued in corresponding European Patent Application No. 14153784.5 dated Jul. 20, 2015, 6 pp.

\* cited by examiner

*Primary Examiner* — Michael Pepitone
(74) *Attorney, Agent, or Firm* — Wood, Herron & Evans, LLP

(57) ABSTRACT

The dental resin modified glass-ionomer composition includes an acidic polymer; an acidic polymerizable monomer selected from 4-(meth)acryloxyalkyltrimellitic anhydride, 4-(meth)acryloxyalkyltrimellitic acid, and a combination thereof; a non-acidic polymerizable monomer; a fluoroaluminosilicate glass filler; water; and at least one polymerization initiator system. The dental resin modified glass-ionomer composition is useful for a dental restorative composition, an endodontic composition, and/or an orthodontic composition, and provides significantly enhanced adhesive property toward tooth structure.

20 Claims, No Drawings

DENTAL RESIN MODIFIED GLASS-IONOMER COMPOSITION

FIELD OF THE INVENTION

This invention relates to dental resin modified glass-ionomer compositions that provide enhanced adhesion to tooth structure.

BACKGROUND

Dental cements are used to attach prosthetic devices such as inlays, onlays, crowns, or posts to tooth structures so that a diseased tooth can restore its function and aesthetics. Dental cements can also be used to attach orthodontic devices, such as orthodontic brackets or an orthodontic band, to a tooth structure to correct misalignment of teeth or adjust spaces between teeth. Dental cements can also be used as root canal sealants.

When cementing prosthetic and orthodontic devices to tooth structures, there are a variety of classes of dental cements available to dental practitioners to choose from and they include, for example, (1) a zinc phosphate cement, (2) a zinc carboxylate cement, (3) a zinc oxide eugenol (ZOE) cement, (4) a glass-ionomer cement, (5) a resin cement, and (6) a resin modified glass-ionomer (RMGI) cement. Each type of cement has its own concomitant advantages and shortcomings, as discussed next.

For example, the zinc phosphate cement utilizes the acid-base setting reaction between zinc oxide and phosphoric acid. Generally, the zinc phosphate cement is provided as a powder/liquid system, which requires manual mixing of the powder and liquid components prior to application. Manual mixing can be a messy process and often lacks consistency due to improper weighing/rationing of powder and liquid components. In addition, zinc phosphate cements have poor adhesive strength to tooth structure, high optical opacity (poor aesthetics), and have a high solubility in the oral environment. Zinc phosphate cements also possess a substantially low initial pH, which can cause irritation or sensitivity during early stages of setting.

The zinc carboxylate cement utilizes the acid-base setting reaction between zinc oxide and polycarboxylic acid. Comparatively, zinc carboxylate cements are gentler to pulp tissue and have improved adhesive property toward tooth structure, as compared to their zinc phosphate counterparts. However, zinc carboxylate cements have a short working time, high optical opacity, low mechanical strength, and require an additional conditioning step prior to cementation.

The zinc oxide eugenol (ZOE) cement utilizes the acid-base setting reaction between zinc oxide and eugenol in the presence of water to form a zinc eugenolate chelate. A ZOE cement has low mechanical strength, poor adhesive properties, poor aesthetics, and high solubility in water, thereby making it suitable for use only as a provisional or temporary cement.

The resin cement utilizes the free-radical polymerization setting reaction of methacrylate monomers. Resin cements are generally reinforced with inorganic glass fillers and possess very good mechanical strength, favorable aesthetic properties, and low solubility in water. Resin cements demonstrate excellent bond strengths to tooth structure, when used in combination with a bonding agent. As a result, resin cements are best suited for cementing aesthetic, yet brittle ceramic restorations. Nevertheless, resin cements are rather hydrophobic and sensitive to water/saliva contamination. Resin cements are also quite technique sensitive and have the potential to cause post-operative sensitivity due to their complicated bonding protocol requiring a separate bonding agent.

The glass-ionomer cement utilizes the acid-base setting reaction between a polycarboxylic acid and a fluoroaluminosilicate glass filler. In comparison to the zinc phosphate cements, the glass-ionomer cements generally demonstrate improved adhesive property, reduced solubility in water, improved mechanical strength, and have the added benefit of cariogenic properties due to long-term sustained release of fluoride. However, the setting reaction is quite sensitive to water/moisture contamination as well as desiccation during the early stage of setting. When compared to resin cements, the glass-ionomer cements are quite brittle, and their bond strength to tooth structure is substantially lower.

Various efforts have been made to combine resin cement chemistry with glass-ionomer cement chemistry to form resin modified glass-ionomer (RMGI) cements. Akahane et al. (U.S. Pat. No. 5,063,257) incorporated polymerizable monomers, a photoinitiator, a surfactant, and a reducing agent into a glass-ionomer composition to make the resulting RMGI composition curable through both an acid-base reaction and a free-radical photo-polymerization. Mitra et al. (U.S. Pat. Nos. 5,130,347 and 5,925,715) incorporated a photoinitiator system into a glass-ionomer composition and added polymerizable groups to the polycarboxylic acid through an amide linkage, to make the resulting RMGI composition curable through both an acid-base reaction and a free radical photo-polymerization. Jandourek (EP 0,329,268A2) incorporated a photoinitiator system, polymerizable monomers, and a polymerizable polycarboxylic acid into a glass-ionomer composition to make the resulting RMGI composition curable through both an acid-base reaction and a free radical photo-polymerization. Mitra et al. (U.S. Pat. No. 5,154,762) incorporated a redox initiator system, along with polymerizable monomers and polymerizable polycarboxylic acid, into a glass-ionomer composition to make the resulting RMGI composition curable through an acid-base reaction and a free radical polymerization, either by a photoinitiator or a redox initiator system. Nakaseko (U.S. Pat. No. 6,214,101) made a paste/paste RMGI composition by incorporating polymerizable monomers and encapsulated polymerization initiators into a glass-ionomer composition.

Accordingly, RMGI cement compositions combine the setting chemistries from both glass-ionomer cements and resin cements. RMGI cement compositions retain the benefit of sustained long-term fluoride release, and provide improved mechanical strength, fracture toughness, aesthetic properties, and adhesive properties over those of traditional glass-ionomer cements alone. And due to the hydrophilic and self-adhesive nature, RMGI cement compositions are generally less sensitive to moisture/saliva contamination and are less technique sensitive, as compared to resin cements. However, the bond strengths to tooth structure of prior RMGI cement compositions are still significantly lower than a resin cement used in combination with a bonding agent. Accordingly, there is a need to further improve the adhesive properties of RMGI cement compositions.

SUMMARY

The dental resin-modified glass-ionomer compositions in accordance with the embodiments of the present invention provide enhanced adhesive strength towards tooth structure, and a simplified restorative procedure. To that end, embodiments of the present invention provide a dental RMGI composition comprising (a) an acidic polymer having a plurality of acidic functional groups selected from the group consisting of a carboxylic acid, a carboxylic acid anhydride, and a combination thereof, wherein the acidic polymer has a weight average molecular weight in a range of about 3,000 to about 100,000; (b) an acidic polymerizable monomer selected from the group consisting of 4-(meth)acryloxyalkyltrimellitic anhydride, 4-(meth)acryloxyalkyltrimellitic acid, and a combination thereof; (c) a non-acidic polymerizable monomer having at least one polymerizable group selected from the group consisting of an acrylate, a methacrylate, an acrylamido, a methacrylamido, and a vinyl group; (d) a fluoroaluminosilicate glass filler; (e) water; and (f) at least one polymerization initiator system selected from the group consisting of a photoinitiator system, a redox initiator system, an alkali aromatic sulfinate, and a combination thereof.

According to another embodiment of the present invention, a dental resin modified glass-ionomer composition kit is provided, the kit comprising the components (a)-(f) of the above composition, a first part including at least the fluroaluminosilicate filler (d), and a second part separately packaged from the first part including at least the acidic polymer (a) and the acidic polymerizable monomer (b). Components (c), (e), and (f) are included in one or both parts. The kit further includes instructions for homogeneously mixing the first part with the second part to form a mixed resin modified glass-ionomer composition and applying the mixed resin modified glass-ionomer composition to a dental substrate.

These and other aspects of the present invention will be more readily apparent from the following detailed description and appended claims.

DETAILED DESCRIPTION OF EMBODIMENTS OF THE INVENTION

Unless specified otherwise, as used herein, the term "(meth)acrylate" refers to "acrylate" or "methacrylate;" the term "(meth)acrylamido" refers to "acrylamido" or "methacrylamido;" and the term "(meth)acryloxy" refers to "acryloxy" or "methacryloxy."

Embodiments of the present invention are directed to dental RMGI compositions that include an acidic polymer, an acidic polymerizeble monomer, a non-acidic polymerizable monomer, a fluoroaluminosilicate glass filler, water, and at least one polymerization initiator system. According to another embodiment of the invention, the dental RMGI compositions may be provided as a kit to maintain separation of various reactive components. Upon mixing of the components of the dental RMGI composition, the resulting mixture is suitable for use in a variety of direct and indirect dental applications, including but not limited to fillings, orthodontic retainers, bridges, space maintainers, tooth replacement appliances, dentures, crowns, posts, jackets, inlays, onlays, facings, veneers, facets, implants, abutments, cements, bonding agents, and splints, and provide improved bonding strengths to dental substrates, such as dentin, enamel, dental alloy, zirconia, ceramic material, or porcelain, and yet maintain other desirable properties.

More specifically and in accordance with the present invention, the dental RMGI compositions include:

(a) an acidic polymer having a plurality of acidic functional groups selected from the group consisting of a carboxylic acid, a carboxylic acid anhydride, and a combination thereof, wherein the acidic polymer has a weight average molecular weight in a range of about 3,000 to about 100,000;

(b) an acidic polymerizable monomer selected from the group consisting of 4-(meth)acryloxyalkyltrimellitic anhydride, 4-(meth)acryloxyalkyltrimellitic acid, and a combination thereof;

(c) a non-acidic polymerizable monomer having at least one polymerizable group selected from the group consisting of an acrylate, a methacrylate, an acrylamido, a methacrylamido, and a vinyl group;

(d) a fluoroaluminosilicate glass filler;

(e) water; and (f) at least one polymerization initiator system selected from the group consisting of a photoinitiator system, a redox initiator system, an alkali aromatic sulfinate, and a combination thereof.

For component (a), at least one acidic polymer is used in the dental RMGI composition. The acidic polymer includes a plurality of acidic functional groups selected from the group consisting of a carboxylic acid, a carboxylic acid anhydride, and a combination thereof. The acidic polymer is characterized as having a weight average molecular weight in the range of about 3,000 to about 100,000, where the weight average molecular weight is measured by gel permeation chromatography (GPC) using polyacrylic acids of various known molecular weights as standards. In another embodiment, the acidic polymer has a weight average molecular weight in the range of about 5,000 to about 100,000. For example, the weight average molecular weight of the acidic polymer can be about 5,000, about 10,000, about 15,000, about 25,000, about 35,000, about 45,000, about 55,000, about 75,000, or in a range between combinations of the foregoing.

In one embodiment, component (a) includes at least one homopolymer or copolymer of an $\alpha,\beta$-unsaturated carboxylic acid or carboxylic acid anhydride. Exemplary monomeric $\alpha,\beta$-unsaturated carboxylic acids or carboxylic acid anhydrides include, but are not limited to, acrylic acid, maleic acid, maleic anhydride, fumaric acid, itaconic acid, itaconic anhydride, aconitic acid, aconitic anhydride, mesaconic acid, citraconic acid, citraconic anhydride, glutaconic acid, glutaconic anhydride. For example, the acidic polymer can include a homopolymer of one of the foregoing exemplary $\alpha,\beta$-unsaturated carboxylic acids or carboxylic acid anhydrides, or a copolymer of two or more of the foregoing exemplary $\alpha,\beta$-unsaturated carboxylic acids or carboxylic acid anhydrides.

According to one embodiment, component (a) is a polymerizable acidic polymer having a plurality of ethylenically unsaturated groups selected from the group consisting of an acrylate, a methacrylate, an acrylamido, a methacrylamido, a vinyl group, and combinations thereof. Suitable polymerizable acidic polymers include those disclosed in Mitra, U.S. Pat. No. 5,130,347. In one embodiment, the polymerizable acidic polymer comprises a homopolymer or a copolymer of a monomeric acid selected from the group consisting of acrylic acid, maleic acid, maleic anhydride, fumaric acid, itaconic acid, itaconic anhydride, aconitic acid, aconitic anhydride, mesaconic acid, citraconic acid, citraconic anhydride, glutaconic acid, glutaconic anhydride, and combinations thereof, where the ethylenically unsaturated groups are covalently attached to the homopolymer or the copolymer via at least a portion of the plurality of acidic functional groups.

For example, according to one embodiment, the polymerizable groups are attached to the polymer or copolymer by reacting a suitably reactive functional group that is bonded to the ethylenically unsaturated moiety with the carboxylic acid anhydride functional group on the polymer or copolymer. Furthermore, in one embodiment, part or all of the remaining carboxylic acid anhydride groups are converted into carboxylic acid groups.

In one embodiment, the polymerizable acidic polymer is a reaction product of a hydroxyalkyl(meth)acrylate with a copolymer of acrylic acid and a monomer selected from group consisting of itaconic anhydride, maleic anhydride, citraconic anhydride, aconitic anhydride, and glutaconic anhydride, or a combination thereof. According to this embodiment, the (meth)acrylate groups are attached to the polymer through ester linkages resulting from the reaction of the hydroxyl groups of the hydroxyalkyl(meth)acrylate with the anhydride groups. Exemplary polymerizable acidic polymers include the reaction product of hydroxyethyl(meth) acrylate with a copolymer of acrylic acid and a monomer selected from group consisting of itaconic anhydride, maleic anhydride, citraconic anhydride, aconitic anhydride, and glutaconic anhydride, or a combination thereof. Other exemplary polymerizable acidic polymers include a reaction product of hydroxyethyl(meth)acrylate with a copolymer of acrylic acid and itaconic anhydride; or a reaction product of hydroxyethyl(meth)acrylate with a copolymer of acrylic acid and maleic anhydride. In one embodiment, the (meth)acrylate groups are attached to the polymer or copolymer through only a portion of the available carboxylic acid anhydride groups, thereby providing the polymer or copolymer with a plurality of anhydride groups. In another embodiment, the (meth)acrylate groups are attached to only a portion of the available anhydride groups, while the remaining anhydride groups are either partially or fully converted to carboxylic acid groups.

According to embodiments of the present invention, the acidic polymer (a) may be present in an amount of about 0.5 wt % to about 50 wt % of the dental RMGI composition, wherein the wt % is based on the total weight of the dental RMGI composition. In one embodiment, the acidic polymer (a) may be present in an amount of about 1 wt % to about 30 wt % of the dental RMGI composition. In one embodiment, the acidic polymer (a) may be present in an amount from about 2 wt % to about 20 wt % of the dental RMGI composition.

For component (b), at least one acidic polymerizable monomer is used in the dental RMGI composition. According to embodiments of the present invention, the acidic polymerizable monomer is selected from the group consisting of 4-(meth)acryloxyalkyltrimellitic anhydride, 4-(meth)acryloxyalkyltrimellitic acid, and combinations thereof. Component (b) provides significantly improved adhesive property to the glass-ionomer composition. In one embodiment, the acidic polymerizable monomer (b) is selected from the group consisting of 4-(meth)acryloxyethyltrimellitic anhydride, 4-(meth)acryloxypropyltrimellitic anhydride, 4-(meth)acryloxybutyltrimellitic anhydride, 4-(meth)acryloxyethyltrimellitic acid, 4-(meth)acryloxypropyltrimellitic acid, 4-(meth)acryloxybutyltrimellitic acid, and combinations thereof. In another embodiment, the acidic polymerizable monomer (b) is selected from the group consisting of 4-methacryloxyethyltrimellitic anhydride, 4-methacryloxyethyltrimellitic acid, and a combination thereof. According to embodiments of the present invention, the acidic polymerizable monomer (b) may be present in an amount from about 0.5 wt % to about 50 wt % based on the total weight of the dental RMGI composition. For example, the acidic polymerizable monomer (b) may be present in an amount from about 1 wt % to about 30 wt % of the dental RMGI composition. In another embodiment, the acidic polymerizable monomer (b) may be present in an amount from about 2 wt % to about 20 wt % of the dental RMGI composition.

For component (c), at least one non-acidic polymerizable monomer is used in the dental RMGI composition. According to embodiments of the present invention, the non-acidic polymerizable monomer includes at least one polymerizable group selected from the group consisting of an acrylate, a methacrylate, an acrylamido, a methacrylamido, and a vinyl group. In one embodiment, the non-acidic polymerizable monomer (c) has at least one polymerizable group selected from the group consisting of an acrylate and a methacrylate. Exemplary polymerizable monomers include, but are not limited to, methyl (meth)acrylate; ethyl (meth)acrylate; propyl (meth)acrylate; butyl (meth)acrylate; hexyl (meth)acrylate; octyl (meth)acrylate; lauryl (meth)acrylate; decyl (meth) acrylate; tridecyl (meth)acrylate; 2-ethoxyethyl (meth)acrylate; 2'-ethoxy-2-ethoxyethyl (meth)acrylate; hydroxyethyl (meth)acrylate; hydroxypropyl (meth)acrylate; hydroxybutyl (meth)acrylate; glycerol di(meth)acrylate; glycerol mono (meth)acrylate; ethyleneglycol di(meth)acrylate; diethyleneglycol di(meth)acrylate; triethyleneglycol di(meth)acrylate (TEGDMA); tetraethyleneglycol di(meth)acrylate; polyethyleneglycol mono-(meth)acrylate; polyethyleneglycol di-(meth)acrylate; polypropyleneglycol mono-(meth) acrylate; polypropyleneglycol di-(meth)acrylate; polytetramethyleneglycol mono-(meth)acrylate; polytetramethyleneglycol di-(meth)acrylate; hexanediol di(meth)acrylate; trimethyloylpropane tri(meth)acrylate; the reaction product of 2-hydroxyethyl methacrylate with 2,4,4-trimethylhexane diisocyanate (UDMA); 2,2-bis[4-(2-hydroxy-3-methacryloylpropoxy)-phenyl]-propane (Bis-GMA); ethoxylated bisphenol A dimethacrylate ("EBPADMA-n", n=total number of moles of ethylene oxide in the molecule, for example 2-20 units); tetrahydrofurfuryl (meth)acrylate; N,N'-methylenebis(acrylamide); N,N'-ethylenebis(acrylamide); N,N'-butylenebis(acrylamide); or a combination thereof. According to another embodiment, the non-acidic polymerizable monomer (c) includes at least one hydroxyl group and at least one ethylenically unsaturated group. Examples of polymerizable monomers having at least one hydroxyl group and at least one ethylenically unsaturated group include, but are not limited to, the following: hydroxyethyl (meth)acrylate; hydroxypropyl (meth)acrylate; hydroxybutyl (meth)acrylate; glyceryl di(meth)acrylate; glyceryl mono(meth)acrylate; 2-hydroxyethoxyethyl (meth) acrylate; 2,2-bis[4-(2-hydroxy-3-methacryloylpropoxy)-phenyl]-propane; or combinations thereof. According to embodiments of the present invention, the non-acidic polymerizable monomer (c) may be present in an amount from about 0.5 wt % to about 50 wt % based on the total weight of the dental RMGI composition. For example, in one embodiment, the non-acidic polymerizable monomer (c) may be present in an amount from about 1 wt % to about 40 wt % of the dental RMGI composition. In another embodiment, the non-acidic polymerizable monomer (c) may be present in an amount from about 2 wt % to about 30 wt % of the dental RMGI composition.

For component (d), at least one fluoroaluminosilicate glass filler is used in the dental RMGI composition. Fluoroaluminosilicate glass fillers are ionically reactive towards acids, such as the acidic polymer (a) or the acidic polymerizable monomer (b). As used herein, "ionically reactive" means when the finely divided fluoroaluminosilicate glass filler (d) and the acidic polymer (a) and/or the acidic polymerizable monomer (b) are mixed together in the presence of water (e), either a viscosity increase or hardening of the mixed composition can be observed. According to embodiments of the present invention, the fluoroaluminosilicate glass filler is a finely divided filler with mean particle size in the range of about 0.02 microns to about 20 microns. The mean particle size of the finely divided fluoroaluminosilicate glass filler can be measured by a conventional particle size measurement instrument that employs laser light scattering methodology. An example of such instrument is a Horiba Model 910 Laser Scattering Particle Size Analyzer (Horiba Inc., Irvine, Calif.). In one embodiment, the mean particle size of the finely divided fluoroaluminosilicate glass filler is in the range from about 0.10 microns to about 10 microns. According to one aspect, the finely divided fluoroaluminosilicate glass filler can further contain calcium, strontium, barium, a rare earth metal, zirconium, zinc, and combinations thereof. Exemplary rare earth metals include, but are not limited to, ytterbium, yttrium, or combinations thereof. In one embodiment, the surface of the fluoroaluminosilicate glass filler is treated or coated with a coupling agent to enhance the interfacial bonding between the filler and resin matrix and improve mechanical properties. In one embodiment, the coupling agent is a silane compound having at least one polymerizable group selected from the group consisting of an acrylate, a methacrylate, an acrylamido, a methacrylamido, and a vinyl group. Useful examples of coupling agents include, but are not limited to, γ-methacryloyloxypropyl trimethoxysilane (MPTMS), γ-methacryloyloxypropyl triethoxysilane, γ-methacryloyloxypropyl methyldimethoxysilane, vinyltrimethoxysilane, and vinyltriethoxysilane. Another useful example of a coupling agent is a compound that has an acid functional group and a polymerizable group selected from the group consisting of an acrylate, a methacrylate, an acrylamido, a methacrylamido, and a vinyl group. Useful examples include, but are not limited to, acrylic acid, methacrylic acid, and maleic acid. According to embodiments of the present invention, the fluoroaluminosilicate glass filler (d) may be present in the dental RMGI composition in an amount from about 1 wt % to about 85 wt % based on the total weight of the dental RMGI composition. For example, in one embodiment, the fluoroaluminosilicate glass filler (d) may be present in an amount from about 5 wt % to about 80 wt % of the dental RMGI composition. In another embodiment, the fluoroaluminosilicate glass filler (d) may be present in an amount from about 20 wt % to about 80 wt % of the dental RMGI composition.

For component (e), water provides a medium needed for the ionic acid-base reaction to take place between the acidic polymer (a) and/or the acidic polymerizable monomer (b), and the fluoroaluminosilicate glass filler (d). According to embodiments of the present invention, water (e) may be present in an amount from about 0.5 wt % to about 40 wt % based on the total weight of the dental RMGI composition. For example, in one embodiment, water (e) may be present in an amount from about 1.0 wt % to about 30 wt % of the dental RMGI composition. In another embodiment, water (e) may be present in an amount from about 2.0 wt % to about 25 wt % of the dental RMGI composition.

For component (f), at least one polymerization initiator system is used in the dental RMGI composition. According to embodiments of the present invention, the polymerization initiator system can be a photoinitiator system, a redox initiator system, an alkali aromatic sulfinate, and combinations thereof. In one embodiment, a photoinitiator is incorporated in the composition. The photoinitiator can be any compound or combination of compounds that can generate free radicals upon exposure to a light source and cause the polymerization or hardening of the composition. The light source can be any dental curing light that emits light in the visible or ultraviolet range. Examples of photoinitiators include, but are not limited to, diketone compounds; benzoin; benzoin ethers and esters; 2,2-diethoxy acetophenone; monoacylphosphine oxide; bisacylphosphine oxide as disclosed in Ellrich et al., U.S. Pat. No. 4,792,632; diaryliodonium salt; triarylsulfonium salt; and any mixture of photoinitiators. Examples of diketone compounds include, but are not limited to, camphorquinone and 1-phenyl-1,2-propanedione. Additionally, a co-initiator can be used together with a photoinitiator to enhance curing efficiency. Co-initiators include tertiary amine and sulfinate compounds. Exemplary co-initiators include, but are not limited to, ethyl 4-(N,N-dimethylamino) benzoate; 4-(N,N-dimethylamino) benzoic acid; 4-(N,N-dimethylamino) benzonitrile; 4-(N,N-dimethylamino) benzaldehyde; 2-(ethylhexyl)-4-(N,N-dimethylamino) benzoate; N,N-dimethylaminoethyl methacrylate; N,N-dimethylaminophenethyl alcohol; sodium benzenesulfinate; and sodium toluenesulfinate. According to one embodiment, the photoinitiator system includes a combination of camphorquinone and a tertiary amine, such as ethyl 4-(N,N-dimethylamino) benzoate; 4-(N,N-dimethylamino) benzoic acid; 4-(N,N-dimethylamino) benzonitrile; 4-(N,N-dimethylamino) benzaldehyde; 2-(ethylhexyl)-4-(N,N-dimethylamino) benzoate; N,N-dimethylaminoethyl methacrylate; and N,N-dimethylaminophenethyl alcohol. In another embodiment, a photoinitiator system includes the combination of camphorquinone and bisacylphosphine oxide or monoacylphosphine oxide. In another embodiment, a photoinitiator system includes the combination of camphorquinone, a tertiary amine, and bisacylphosphine oxide or monoacylphosphine oxide. According to embodiments of the present invention, the photoinitiator may be present in an amount from about 0.01 wt % to about 10 wt % based on the total weight of the dental RMGI composition. For example, the photoinitiator may be present in an amount from about 0.05 wt % to about 5 wt % of the dental RMGI composition.

According to another embodiment, a redox initiator system is incorporated in the dental RMGI composition. A redox initiator system usually comprises at least one reducing agent and at least one oxidizing agent. When the reducing agent and the oxidizing agent are mixed together, a redox reaction proceeds that generates free radicals and initiates the polymerization of monomers, resulting in the curing or hardening of the mixed composition. Any pair of reducing agent and oxidizing agent can be used as long as they can effectively initiate the polymerization of the monomers.

The reducing agents include, but are not limited to, aromatic sulfinate salt; aliphatic sulfinate salt; thiourea; substituted thiourea; Fe(II) salt; Cu(I) salt; Co(II) salt; ascorbic acid; ascorbic acid derivatives and salts; barbituric acid; and barbituric acid derivatives and salts. In one embodiment, the reducing agent is a substituted thiourea. Substituted thioureas include, but are not limited to, 1-(2-pyridyl)-2-thiourea; 1-acetyl-2-thiourea; 1-(2-tetrahydrofurfuryl)-2-thiourea; 1-benzoylthiourea; 1-benzoyl-3-phenylthiourea; and 1,1,3,3-tetramethylthiourea. In one embodiment, the reducing agent is selected from the group consisting of barbituric acid, a barbituric acid derivative, a salt of barbituric acid, and a combination thereof. In another embodiment, the reducing agent is selected from the group consisting of ascorbic acid, an ascorbic acid derivative, a salt of ascorbic acid, and a combination thereof. According to embodiments of the present invention, the reducing agent or agents may be present in an amount from about 0.01 wt % to about 10 wt % based on the total weight of the dental RMGI composition. For example, the reducing agent(s) may be present in an amount from about 0.1 wt % to about 3 wt % of the dental RMGI composition.

The oxidizing agents include, but are not limited to, a tertiary hydroperoxide compound with at least one hydroperoxide group attached to at least one tertiary carbon; a Cu(II) salt, such as Cu(II) acetylacetonate, Cu(II) benzoylacetonate, or Cu(II) cyclohexylbutyrate; a Fe(III) salt, such as $FeCl_3$, Fe(III) benzoyl acetonate, or Fe(III) cyclohexylbutyrate; a Co(III) salt; persulfate salt; permanganate salt; and combinations of these. In one embodiment, tertiary hydroperoxide compounds are used. Examples of tertiary hydroperoxide compounds include, but are not limited to, t-butyl hydroperoxide; t-amyl hydroperoxide; p-diisopropylbenzene hydroperoxide; cumene hydroperoxide; pinane hydroperoxide; p-methane hydroperoxide; and 1,1,3,3-tetramethylbutyl hydroperoxide. In one embodiment, the oxidizing agent is selected from the group consisting of persulfate salt, permanganate salt, and a combination thereof. Examples of persulfate salt include, but are not limited to potassium persulfate, sodium persulfate, lithium persulfate, and ammonium persulfate. According to embodiments of the present invention, the oxidizing agent or agents may be present in an amount of about 0.01 wt % to about 10 wt % based on the total weight of the dental RMGI composition. For example, the total oxidizing agent or agents may be present in an amount from about 0.1 wt % to about 5 wt % of the dental RMGI composition.

In one embodiment, a sulfinate salt compound is incorporated as an initiator. An aromatic sulfinate salt and/or an aliphatic sulfinate salt can be used. Examples of aromatic sulfinate salt include, but are not limited to, sodium benzenesulfinate, lithium benzenesulfinate, sodium p-toluenesulfinate, and lithium p-toluenesulfinate.

The photoinitiator system, redox initiator system, and sulfinate salt compound can be incorporated alone or in combination with each other. In one embodiment, a combination of a photoinitiator system and a redox initiator system are used in the composition. In another embodiment, a combination of a photoinitiator and a sulfinate salt compound are used in the composition. In another embodiment, a photoinitiator, a redox initiator, and a sulfinate salt are all incorporated in the composition.

According to one embodiment, the dental RMGI composition may further comprise component (g) at least one finely divided filler that is not ionically reactive towards the acidic polymer (a) or the acidic polymerizable monomer (b). Examples of fillers that are not ionically reactive towards acidic moieties include, but are not limited to, an inorganic salt, fluoride, silicate glass, aluminosilicate glass, aluminoborosilicate glass, quartz, silica, zirconia, zirconia-silica, or a polymeric filler. In one embodiment, the finely divided filler (g) that is not ionically reactive towards the acidic polymer (a) or the acidic polymerizable monomer (b) is selected from the group consisting of strontium fluoride, ytterbium fluoride, yttrium fluoride, barium sulfate, barium tungstate, zirconium oxide, quartz, silica, and polymeric filler. Suitable silica fillers include fumed silica, colloidal silica, and/or precipitated silica. Examples of silica fillers include Aerosil® series such as OX-50, OX-130, and OX-200 silica sold by Degussa (Ridgefield Park, N.J.), and Cab-O-Sil® M5 and Cab-O-Sil® TS-530 silica sold by Cabot Corp (Tuscola, Ill.). The finely divided filler (g) may also include nanoparticles such as those obtained through a sol-gel process. Mixtures of different fillers can be used. In one embodiment, the finely divided filler (g) is an inorganic filler that is radiopaque for increased x-ray contrast ability. Examples of radiopaque inorganic fillers include metals, salts, oxides, fluorides, silicate glass, aluminosilicate glass, aluminoborosilicate glass, and fluoroaluminosilicate glass containing elements of high atomic number such as Sr, Y, Zr, Ba, La, Hf, Zn, Bi, W, rare earth metals, and combinations of these.

In one aspect, the surface of the inorganic filler may be treated or coated with a coupling agent to enhance the interfacial bonding between the filler and resin matrix and improve mechanical properties. In one embodiment, the coupling agent is a silane compound having at least one polymerizable group selected from the group consisting of an acrylate, a methacrylate, an acrylamido, a methacrylamido, and a vinyl group. Useful examples of coupling agents include, but are not limited to, γ-methacryloyloxypropyl trimethoxysilane (MPTMS), γ-methacryloyloxypropyl triethoxysilane, γ-methacryloyloxypropyl methyldimethoxysilane, vinyltrimethoxysilane, and vinyltriethoxysilane.

According to one embodiment, the finely divided filler (g) is a polymeric filler. The polymeric filler may comprise about 5% to about 100% by weight of a polymeric matrix and about 0% to about 95% by weight of at least one inorganic filler. In one embodiment, the polymeric matrix comprises one or more thermoset materials. As an example, the polymeric filler can be obtained by grinding a polymer or polymeric composite to fine particles with a mean particle size of more than about 1.0 micron and less than about 50 microns. In one embodiment, the polymeric filler has a mean particle size of more than about 2 microns and less than about 30 microns. In one embodiment, the finely divided filler (g) may be present in an amount from about 0.5 wt % to about 70 wt % based on the total weight of the dental RMGI composition. For example, in one embodiment, component (g) may be present in an amount from about 1 wt % to about 60 w % of the dental RMGI composition. In one embodiment, component (g) may be present in an amount from about 2 wt % to about 50 wt % of the dental RMGI composition.

In one embodiment, the dental RMGI composition optionally further comprises a non-polymeric acidic compound free of any polymerizable group, such as multi-basic acids. Examples include, but are not limited to, tartaric acid and citric acid.

In one embodiment, the dental RMGI composition further comprises a component (h) selected from the group consisting of a polymerization inhibitor, a UV stabilizer and a colorant, and combinations thereof. The polymerization inhibitor is a stabilizer that improves the shelf stability of the restorative material. The most commonly used stabilizers include 2,6-di-(tert-butyl)-4-methylphenol (BHT) and 4-methoxyphenol (MEHQ). The UV stabilizer is used to improve the color stability of the restorative material upon exposure to UV light. An examplary UV stabilizer is 2-hydroxy-4-methoxybenzophenone (UV-9). The colorants may be used to achieve a desired shade and can be inorganic pigments or organic dyes.

In one embodiment, the dental RMGI composition optionally further comprises a polymerizable monomer having at least one acidic group selected from the group consisting of a sulfonic acid, a sulfinic acid, a phosphoric acid, a phosphonic acid, and a phosphate group.

According to embodiments of the present invention, the dental RMGI composition is a multi-part composition with each part selected from the group consisting of a powder, liquid and paste. In one embodiment, the composition is a two-part powder/liquid composition with the first part in a powder form and comprising component (d), and the second part in a liquid form and comprising components (a), (b), (c), and (e); wherein the polymerization initiator (f) can be in the first part, the second part, or both parts. The first part can further comprise a component selected from the group consisting of an acidic polymer (a), which can be the same or different from (a) in the second part; an acidic polymerizable monomer (b), which can be the same or different from (b) in the second part; and a combination thereof. In one embodiment, the two-part powder/liquid composition further comprises at least one finely divided filler (g) that is not ionically reactive towards the acidic polymer (a) or the acidic polymerizable monomer (b). In one embodiment, the two-part powder/liquid composition further comprises at least one component (h) selected from the group consisting of a polymerization inhibitor, a UV stabilizer and a colorant, and the combination thereof.

In another embodiment, the dental RMGI composition is a two-part paste/paste composition with the first paste comprising components (a), (b), (e), and at least one finely divided filler (g) that is not ionically reactive towards (a) or (b); and the second paste comprising (c) and (d), wherein the polymerization initiator system (f) can be incorporated in one or both pastes. In another embodiment, the first paste can further comprise a non-acidic polymerizable monomer (c), which can be the same or different from (c) in the second paste. If the polymerization initiator system (f) is a redox initiator system, the oxidizing agent may be incorporated in the first paste comprising (a) and (b), while the reducing agent is incorporated into the second paste comprising (c) and (d). One or more components of the polymerization initiator system (f) can be microencapsulated with a water soluble encapsulant. If one or both components of the redox initiator system are encapsulated, then both the reducing agent and the oxidizing agent can be incorporated into the second paste. In another embodiment, the two-part paste/paste dental RMGI composition further comprises at least one component (h) selected from the group consisting of a polymerization inhibitor, a UV stabilizer and a colorant, and the combination thereof. The two pastes can be mixed in any volume ratio. In one embodiment, the two pastes are mixed in a volume ratio between about 10:1 to about 1:10. In one embodiment, the two pastes are mixed in 1:1 volume ratio.

The two parts need to be mixed just prior to application, applied to a dental substrate, and hardened inside a patient's mouth by self-curing or the combination of self-curing or light-curing.

Thus, the components (a)-(f), and optional components (g)-(h), may be provided as a kit.

The dental RMGI composition of present invention is useful in formulating restorative materials such as a cavity filling material, a cement, a base/liner, or a pit/fissure sealant. The dental RMGI compositions of embodiments of the present invention are also useful in formulating orthodontic materials such as an orthodontic adhesive or a cement. The dental RMGI compositions of embodiments of the present invention are also useful in formulating endodontic materials such as a sealing or filling material.

According to another embodiment of the present invention, a dental restorative method is provided. The method includes preparing the dental RMGI composition in accordance with embodiments of the present invention described above by homogenously mixing at least the components (a)-(f) just prior to application; applying the mixed dental RMGI composition to a dental substrate such as dentin, enamel, dental metal alloy, zirconia, ceramic material, and porcelain; and hardening the mixture either by self-curing or the combination of self-curing and photo-curing. The bond strength of the mixed composition to dentin substrate is at least 5 MPa. In one embodiment, the bond strength of the mixed composition to dentin substrate is at least 10 MPa.

This invention is illustrated by the following examples that are merely for the purpose of illustration and are not to be regarded as limiting the scope of the invention or the manner in which it can be practiced. For convenience, individual component amounts are provided as weight percents that are based on the total weight of the composition.

Compressive Strength Testing

The specimens were prepared by filling a mixed composition into a stainless-steel mold with a dimension of 4 mm (diameter)×3 mm (height), and allowed to self-cure in an oven at 37° C. for approximately 60 minutes. The cured disk was removed from the mold and conditioned in water at 37° C. for 24 hours before subjecting the cured disk to mechanical testing on an Instron Universal Tester (Model 4467) in compression mode with a crosshead speed of 0.50 mm/minute. The peak load at which a specimen breaks was used to calculate the compressive strength expressed in MPa unit. Six specimens were tested for each formula.

Bond Strength Testing

For dentin specimens, extracted human teeth (a set of 6 specimens) were embedded in cold-cure acrylics. A diamond saw was used to remove the crown and the exposed dentin surface was polished with 600-grit SiC paper, rinsed with water, and dried with a dental syringe. For enamel specimens, extracted bovine teeth (a set of 6 specimens) were embedded in cold-cure acrylics. The enamel bonding surface was prepared with a fine diamond burr, rinsed with water, and dried with a dental syringe.

The prepared dentin and enamel specimens were then held securely by a bonding jig (Ultradent, Inc.) with a cylindrical mold ($\Phi$=2.38 mm). The mixed composition was directly applied to the dentin or enamel surface inside the mold and self-cured. The bonded assemblies including the bonding jig were conditioned at 37° C. in a high humidity chamber (85-90% relative humidity) for 1 hour. After removing the bonding jig, the bonded specimens were conditioned in water at 37° C. for 24 hours before being subjected to debonding testing on an Instron mechanical tester (Model 4467, Instron Corporation) in shear mode using a notched (semi-circular) edge at a crosshead speed of 1.0 mm/minute. Shear bond strength values in MPa were calculated by dividing the peak load by the bonding area, and averaged for each set.

Only two-part dual-cure paste/paste cement RMGI compositions were formulated and tested in the following examples. Although no examples are given here, other configurations (self-cure vs. dual-cure; cement vs. filling material, liner/base; paste/paste vs. powder/liquid) can be easily obtained by incorporating different curing initiators (self-cure initiator or a combination of self-cure initiator and photo-initiator), filler type (reactive filler and/or non-reactive filler with acid), and viscosity (varying filler concentration).

EXAMPLES

Abbreviations for Materials Used in all Examples 2,6-di-(tert-butyl)-4-methylphenol (BHT); 2,2-bis[4-(2-hydroxy-3-methacryloylpropoxy)-phenyl]-propane (Bis-GMA); camphorquinone (CQ); ethyl 4-(N,N-dimethylamino) benzoate (EDMAB); glyceryldimethacrylate (GDM); hydroxyethyl methacrylate (HEMA); 4-methacryloxyethyltrimellitic anhydride (4-META); 1-(2-pyridyl)-2-thiourea (PTU); strontium zinc fluoroaluminosilicate glass that is surface-treated with γ-methacryloyloxypropyltrimethoxysilane and has a mean particle size of 4.0 microns (FAS Filler); OX-50 fumed silica that is surface treated with γ-methacryloyloxypropyltrimethoxysilane (ST-OX-50); 1,1,3,3-tetramethylbutyl hydroperoxide (TMBHP); surface treated fumed silica or colloidal silica sold by Cabot Corp (TS-530); and the reaction product of HEMA with copolymer of acrylic acid (AA) and itaconic anhydride (IA) with a molar ratio of AA:IA=3.8:1, wherein 70% of anhydride groups are esterified by HEMA and the final polymer has a weight average molecular weight of 15,600 (MA-Poly(AA-IA)).

In preparing the following three examples of a two-part paste/paste RMGI composition that includes a base paste and a catalyst paste, all of the monomers and any other component that is soluble in the resin mixture were first mixed together to make a homogeneous liquid mixture, and then the fillers (TS-530, ST-OX-50, FAS filler) were blended into the homogenous liquid mixture to make the paste. For all the physical testing (gel time, set time, compressive strength, bond strength to dentin and enamel substrates), the base and catalyst pastes were filled in a 1:1 (volume ratio) dual-barrel syringe and mixed using a static mixer. However, other volume ratios can also be used if necessary. Alternatively, mixing can be done manually using a spatula.

The base paste for all three examples was the same (B1) and had the following composition provided in Table I:

TABLE I

| Base Paste Components | Ingredients | B1 % by weight |
|---|---|---|
| Component (c) | Bis-GMA | 3.04 |
| Component (c) | GDM | 10.15 |
| Component (c) | HEMA | 11.32 |
| Component (d) | FAS Filler | 71.71 |
| Component (f) | PTU | 0.51 |
| Component (f) | CQ | 0.08 |
| Component (f) | EDMAB | 0.25 |
| Component (g) | TS530 | 2.93 |
| Component (h) | BHT | 0.03 |

The catalyst pastes for the three examples had different compositions (C1, C2, and C3), as provided in Table II. TMBHP in the catalyst paste and PTU in the base paste constituted a redox initiator system. CQ and EDMAB in the base paste constituted a photoinitiator system.

TABLE II

| Catalyst Paste Components | Ingredients | C1 % by wt | C2 % by wt | C3 % by wt |
|---|---|---|---|---|
| Component (a) | MA-Poly(AA-IA) | 28.01 | 23.31 | 17.05 |
| Component (b) | 4-META | — | 3.89 | 8.89 |
| Component (c) | HEMA | 35.21 | 34.19 | 32.61 |
| Component (e) | De-ionized Water | 16.00 | 15.54 | 14.82 |
| Component (f) | TMBHP | 0.72 | 0.70 | 0.67 |
| Component (g) | ST-OX-50 | 19.92 | 22.24 | 25.83 |
| Component (h) | BHT | 0.14 | 0.13 | 0.13 |

Example 1

Comparative Example 1 comprising base paste (B1) and catalyst paste (C1) was made for comparison purposes, representing the current art. The catalyst paste (C1) contained only the acidic polymer (component (a)), without any acidic polymerizable monomer (component (b)).

When base paste (B1) was mixed with catalyst paste (C1) through a dual-barrel syringe fitted with a static mixer, the mixed material gelled after 1' 55" (1 minute, 55 seconds) and hardened (or set) after 4' 10". The cured composition of Comparative Example 1 had a compressive strength of 120.0±9.5 MPa, and a shear bond strength of 0.0±0.0 MPa to dentin substrate and 0.0±0.0 MPa to enamel substrate. While each of the 6 specimens tested in the comparative experiment failed to yield a measurable shear bond strength, this is not uncommon. For low shear bond strength samples (e.g., <2 MPa), the shear bond test method employed herein can be sensitive to stress introduced during demolding and sample handling, and desiccation during testing. Accordingly, a conservative conclusion is that the shear bond strengths of the Example 1 samples bonded to dentin and enamel substrates was less than 2 MPa.

Example 2

The composition in Example 2 consisted of base paste (B1) and catalyst paste (C2). The catalyst paste (C2) contained 3.89 wt % of the acidic polymerizable monomer (component (b)) in addition to the acidic polymer (component (a)). When base paste (B1) was mixed with catalyst paste (C2) through a dual-barrel syringe fitted with a static mixer, the mixed material gelled after 2' 05 ' and hardened (or set) after 4' 10". The cured composition of Example 2 had a compressive strength of 128.0±11.0 MPa, and a shear bond strength of 9.4±4.3 MPa to dentin substrate and 6.6±5.0 MPa to enamel substrate.

Example 3

The composition in Example 3 consisted of base paste (B1) and catalyst (C3). The catalyst paste (C3) contained 8.89 wt % of acidic polymerizable monomer (component (b)) in addition to the acidic polymer (component (a)). When base paste (B1) was mixed with catalyst paste (C3) through a dual-barrel syringe fitted with a static mixer, the mixed material gelled after 2' 12" and hardened (or set) after 4' 18". The cured composition of Example 3 had a compressive strength of 123.6±13.9 MPa, and a shear bond strength of 16.5±3.1 MPa to dentin substrate and 15.7±6.0 MPa to enamel substrate.

The above Examples 1-3 illustrate the usefulness of the inventive dental RMGI composition comprising both an acidic polymer and an acidic polymerizable monomer, providing significantly enhanced adhesive property toward tooth structure over current art. In particular, the combination of the acidic polymer and the acidic polymerizable monomer provided comparable compressive strength while increasing the shear bond strength to both dentin and enamel as compared to a prior art composition containing only the acidic polymer. More specifically, while the prior art example exhibited a shear bond strength of less than 2 MPa, compositions according to the present invention exhibit a shear bond strength to dentin of at least 5 MPa, and even greater than 10 MPa. The higher bond strength in Example 3 was achieved by increasing the amount of the acidic polymerizable monomer (b) relative to the amount of the acidic polymer (a), with a similar total content of (a)+(b). The ratio of (a):(b) in Example 2 was roughly 6:1, while the ratio of (a):(b) in Example 3 was roughly 2:1, and the effect was not quite doubling the adhesion to dentin and more than doubling the adhesion to enamel. Thus, in one embodiment of the invention, the ratio of (a):(b) may be about 1:1 to about 8:1, for example, about 1:1, about 1.5:1, about 2:1, about 2:5:1, about 3:1, about 4:1, about 5:1, about 6:1, about 7:1, about 8:1 and the like, or in a range between combinations of the foregoing, such as about 1.5:1 to about 4:1. In another embodiment of the invention, the ratio of (a):(b) may be about 1:4 to about 1:1, for example, about 1:4, about 1:3, about 1:2.5, about 1:2 and the like.

The dental RMGI composition of the current invention can be used as a dental restorative composition, an endodontic composition, and an orthodontic composition. Useful restorative compositions of the current invention could be a dental cavity filling material, a cement, a liner, a base, and a pit/fissure sealant composition. Useful endodontic compositions could be an endodontic sealing and/or filling composition for the sealing and filling a root canal or cement for post cementation. Useful orthodontic compositions could be an orthodontic adhesive or cement composition for adhering an orthodontic appliance to tooth surfaces. In one embodiment, the dental RMGI composition of the current invention is a dental cement composition.

In one embodiment, the dental RMGI composition of the current invention is a dental cavity filling composition. In one embodiment, the dental RMGI composition of the current invention is a dental cavity liner or base composition. In one embodiment, the dental RMGI composition of the current invention is a dental pit/fissure sealant composition.

While the present invention has been illustrated by the description of one or more embodiments thereof, and while the embodiments have been described in considerable detail, they are not intended to restrict or in any way limit the scope of the appended claims to such detail. Additional advantages and modifications will readily appear to those skilled in the art. The invention in its broader aspects is therefore not limited to the specific details, representative product and method and illustrative examples shown and described. Accordingly, departures may be made from such details without departing from the scope of the general inventive concept.

What is claimed is:

1. A dental resin modified glass-ionomer composition comprising the components:
   (a) an acidic polymer having a plurality of acidic functional groups selected from the group consisting of a carboxylic acid, a carboxylic acid anhydride, and a combination thereof, wherein the acidic polymer has a weight average molecular weight in a range of about 3,000 to about 100,000;
   (b) an acidic polymerizable monomer selected from the group consisting of 4-(meth)acryloxyalkyltrimellitic anhydride, 4-(meth)acryloxyalkyltrimellitic acid, and a combination thereof;
   (c) a non-acidic polymerizable monomer having at least one polymerizable group selected from the group consisting of an acrylate, a methacrylate, an acrylamido, a methacrylamido, and a vinyl group;
   (d) a fluoroaluminosilicate glass filler;
   (e) water; and
   (f) at least one polymerization initiator system selected from the group consisting of a photoinitiator system, a redox initiator system, an alkali aromatic sulfinate, and a combination thereof,
   wherein the ratio of (a):(b) is about 1:4 to about 4:1.

2. The composition of claim 1, wherein the acidic polymer (a) has a weight average molecular weight in the range of about 10,000 to about 100,000.

3. The composition of claim 1, wherein the acidic polymer (a) comprises a homopolymer or copolymer of an α,β-unsaturated carboxylic acid or carboxylic acid anhydride.

4. The composition of claim 1, wherein the acidic polymer (a) is a homopolymer or a copolymer of a monomeric acid selected from the group consisting of acrylic acid, maleic acid, maleic anhydride, fumaric acid, itaconic acid, itaconic anhydride, aconitic acid, aconitic anhydride, mesaconic acid, citraconic acid, citraconic anhydride, glutaconic acid, glutaconic anhydride, and combinations thereof.

5. The composition of claim 1, wherein the acidic polymer (a) is a polymerizable acidic polymer comprising a plurality of ethylenically unsaturated groups selected from the group consisting of an acrylate, a methacrylate, an acrylamido, a methacrylamido, and a vinyl group.

6. The composition of claim 5, wherein the polymerizable acidic polymer comprises a homopolymer or a copolymer of a monomeric acid selected from the group consisting of acrylic acid, maleic acid, maleic anhydride, fumaric acid, itaconic acid, itaconic anhydride, aconitic acid, aconitic anhydride, mesaconic acid, citraconic acid, citraconic anhydride, glutaconic acid, glutaconic anhydride, and combinations thereof, and wherein the ethylenically unsaturated groups are covalently attached to the homopolymer or the copolymer via at least a portion of the plurality of acidic functional groups.

7. The composition of claim 6, wherein the polymerizable acidic polymer is a reaction product of a hydroxyalkyl(meth)acrylate, with a copolymer of acrylic acid and a monomer selected from group consisting of itaconic anhydride, maleic anhydride, citraconic anhydride, aconitic anhydride, and glutaconic anhydride, and combinations thereof.

8. The composition of claim 1, wherein the acidic polymerizable monomer (b) is selected from the group consisting of 4-(meth)acryloxyethyltrimellitic anhydride, 4-(meth)acryloxypropyltrimellitic anhydride, 4-(meth)acryloxybutyltrimellitic anhydride, 4-(meth)acryloxyethyltrimellitic acid, 4-(meth)acryloxypropyltrimellitic acid, 4-(meth)acryloxybutyltrimellitic acid, and combinations thereof.

9. The composition of claim 1, wherein the acidic polymerizable monomer (b) is selected from the group consisting of 4-methacryloxyethyltrimellitic anhydride, 4-methacryloxyethyltrimellitic acid, and a combination thereof.

10. The composition of claim 1, wherein the fluoroaluminosilicate glass filler (d) has a mean particle size of about 0.02 microns to about 20 microns.

11. The composition of claim 1, wherein the fluoroaluminosilicate glass filler (d) comprises calcium, strontium, barium, a rare earth metal, zirconium, zinc, or a combination thereof.

12. The composition of claim 11, wherein the fluoroaluminosilicate glass filler (d) comprises the rare earth metal selected from ytterbium, yttrium, or a combination thereof.

13. The composition of claim 1, wherein the polymerization initiator system is the redox initiator system comprising a reducing agent and an oxidizing agent.

14. The composition of claim 13, wherein the reducing agent is selected from the group consisting of a substituted thiourea, barbituric acid, a barbituric acid derivative, a salt of barbituric acid, ascorbic acid, an ascorbic acid derivative, a salt of ascorbic acid, and a combination thereof, and wherein the oxidizing agent is a tertiary hydroperoxide, a persulfate salt, a permanganate salt, or a combination thereof.

15. A dental resin modified glass-ionomer composition comprising the components:
   (a) an acidic polymer having a plurality of acidic functional groups selected from the group consisting of a carboxylic acid, a carboxylic acid anhydride, and a combination thereof, wherein the acidic polymer has a weight average molecular weight in a range of about 3,000 to about 100,000;
   (b) an acidic polymerizable monomer selected from the group consisting of 4-(meth)acryloxyalkyltrimellitic anhydride, 4-(meth)acryloxyalkyltrimellitic acid, and a combination thereof;
   (c) a non-acidic polymerizable monomer having at least one polymerizable group selected from the group consisting of an acrylate, a methacrylate, an acrylamido, a methacrylamido, and a vinyl group;
   (d) a fluoroaluminosilicate glass filler;
   (e) water; and
   (f) a redox polymerization initiator system comprising a reducing agent and an oxidizing agent,
   wherein the ratio of (a):(b) is about 1:4 to about 8:1, and wherein the reducing agent is a substituted thiourea and the oxidizing agent is a tertiary hydroperoxide.

16. A dental resin modified glass-ionomer composition kit comprising:
   the components (a)-(f) of the dental glass-ionomer composition of claim 1;

a first part including at least the fluoroaluminosilicate filler (d);

a second part separately packaged from the first part including at least the acidic polymer (a) and the acidic polymerizable monomer (b), wherein components (c), (e), and (f) are included in one or both of the first part and the second part; and instructions for homogeneously mixing the first part with the second part to form a mixed resin modified glass-ionomer composition and applying the mixed resin modified glass-ionomer composition to a dental substrate.

17. The kit of claim 16, wherein the polymerization initiator system (f) comprises a redox initiator system comprising a reducing agent and an oxidizing agent, wherein either the oxidizing agent is in the first part and the reducing agent is in the second part, or the oxidizing agent is in the second part and the reducing agent is in the first part.

18. The kit of claim 16, wherein the first part comprising (d) is a powder, and the second part comprising (a), (b), (c), and (e) is a liquid.

19. The kit of claim 16, wherein the first part comprising (c) and (d) is a paste, and the second part comprising (a),(b), (e), and (g) at least one finely divided filler that is not ionically reactive towards (a) is a paste.

20. A dental resin modified glass-ionomer composition comprising the components:

(a) a polymerizable acidic polymer having a plurality of acidic functional groups selected from the group consisting of a carboxylic acid, a carboxylic acid anhydride, and a combination thereof, and a plurality of ethylenically unsaturated groups selected from the group consisting of an acrylate, a methacrylate, an acrylamido, a methacrylamido, and a vinyl group, wherein the polymerizable acidic polymer has a weight average molecular weight in a range of about 3,000 to about 100,000;

(b) an acidic polymerizable monomer selected from the group consisting of 4-(meth)acryloxyalkyltrimellitic anhydride, 4-(meth)acryloxyalkyltrimellitic acid, and a combination thereof;

(c) a non-acidic polymerizable monomer having at least one polymerizable group selected from the group consisting of an acrylate, a methacrylate, an acrylamido, a methacrylamido, and a vinyl group;

(d) a fluoroaluminosilicate glass filler;

(e) water; and (f) at least one polymerization initiator system selected from the group consisting of a photoinitiator system, a redox initiator system, an alkali aromatic sulfinate, and a combination thereof, wherein the ratio of (a):(b) is about 1:4 to about 8:1.

* * * * *